United States Patent [19]

Scharwaechter et al.

[11] 4,315,931
[45] Feb. 16, 1982

[54] N-PYRIMIDINYL-IMIDOACID ESTERS AND DRUGS CONTAINING THE SAID COMPOUNDS

[75] Inventors: Peter Scharwaechter, Moorrege; Klaus Gutsche, Rellingen; Wilhelm Kohlmann, Moorrege, all of Fed. Rep. of Germany; Gerhard Kroemer, deceased, late of Elmshorn, Fed. Rep. of Germany; by Norma Kroemer, legal representative, Lahn-Giessen by Helmut Kroemer, legal representative; by Maria M. Kroemer, legal representative, both of Stolberg, all of Fed. Rep. of Germany

[73] Assignee: BASF Aktiengesellschaft, Fed. Rep. of Germany

[21] Appl. No.: 921,701

[22] Filed: Jul. 3, 1978

[30] Foreign Application Priority Data

Jul. 6, 1977 [DE] Fed. Rep. of Germany ....... 2730468

[51] Int. Cl.³ .................. C07D 239/48; A61K 31/505

[52] U.S. Cl. .................................... 424/251; 544/298; 544/224; 544/317; 544/319; 544/320; 544/322; 544/327; 544/332; 544/295; 544/296; 544/324; 544/325; 544/408; 546/312; 548/135; 548/197; 548/245; 548/247

[58] Field of Search ............... 544/325, 295, 296, 324; 424/251, 250

[56] References Cited

U.S. PATENT DOCUMENTS

3,049,544  8/1962  Stenbuck et al. .................... 544/325

FOREIGN PATENT DOCUMENTS

336  1/1979  European Pat. Off. ............ 544/325

OTHER PUBLICATIONS

Meerwein, Houben-Weyl, *Methoden der Organischen Chemie*, vol. 6/3, 1965, pp. 317–319.

*Primary Examiner*—Donald G. Daus
*Assistant Examiner*—James H. Turnipseed
*Attorney, Agent, or Firm*—Keil & Witherspoon

[57] ABSTRACT

Unsubstituted or substituted 5-phenyl- and 5-benzyl-4-amino-pyrimidine-2-imidoacid esters, their preparation, drugs containing these compounds, and their use in infectious diseases.

13 Claims, No Drawings

N-PYRIMIDINYL-IMIDOACID ESTERS AND DRUGS CONTAINING THE SAID COMPOUNDS

The present invention relates to novel imidoacid esters of the formula I

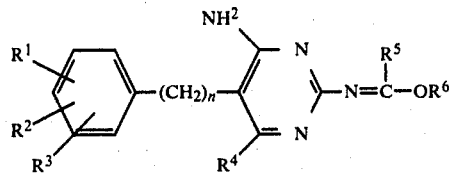
(I)

where $R^1$, $R^2$ and $R^3$, which may be identical or different, are hydrogen, methyl, methoxy or chlorine, $R^4$ is hydrogen or alkyl of 1 to 4 carbon atoms, $R^5$ is alkyl of 1 to 6 carbon atoms or benzyl, $R^6$ is alkyl of 1 to 4 carbon atoms or benzyl and n is 0 or 1.

Preferably, the substituents $R^1$, $R^2$ and $R^3$ are in the 3-, 4- and 5-positions of the benzene ring.

Preferred compounds of the formula I are those where $R^4$ is hydrogen or ethyl.

The compounds according to the invention, of the formula I, are prepared by the conventional methods of preparing imidoacid esters, as described, inter alia, in Houben-Weyl "Methoden der organischen Chemie", volume 6/3, by reacting a compound of the formula II

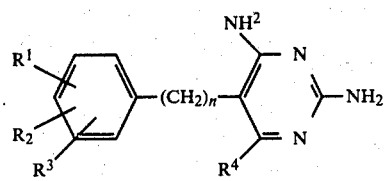
(II)

where $R^1$, $R^2$, $R^3$, $R^4$ and n have the above meanings, with an orthocarboxylic acid ester of the formula III $$R^5—C(OR^6)_3 \quad (III)$$

where $R^5$ and $R^6$ have the above meanings.

The compounds of the formula I may be prepared in the presence or absence of a solvent; in the latter case, an excess of the orthocarboxylic acid ester is employed. Examples of suitable solvents are dimethylformamide and dioxane. The reaction temperatures are from 0° to 150° C., preferably from 50° to 100° C., or up to the boiling point of the solvent, or orthocarboxylic acid ester, employed. The reaction may be carried out in the presence or absence of catalytic amounts of an acid, e.g. hydrochloric acid.

If, for example, 2,4-diamino-5-(3,4,5-trimethoxy-benzyl)-pyrimidine and triethyl orthoacetate are used as starting materials, the course of the reaction can be represented by the following equation:

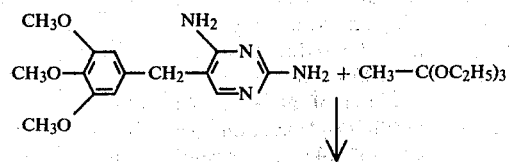

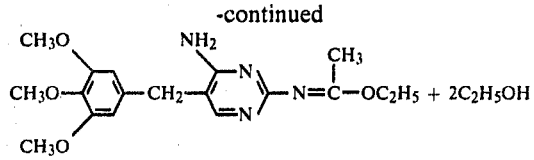

The compounds according to the invention, of the formula I, are antimicrobially active in the case of illnesses caused by bacteria and protozoa and, when combined with sulfonamides, potentiate the antimicrobial action of the latter. They can therefore be used in bacterial illnesses of the respiratory organs, digestive organs and urinary tract, in infections of the throat, nose and ears, in systemic infectious diseases in general, and in malaria.

Examples of suitable sulfonamides are: 2-sulfanilamido-pyridine, 2-sulfanilamido-thiazole, 2-sulfanilamido-pyrimidine, 2-sulfanilamido-4-methyl-pyrimidine, 2-sulfanilamido-4,6-dimethyl-pyrimidine, 4-sulfanilamido-2,6-dimethyl-pyrimidine, 5-sulfanilamido-3,4-dimethyl-isoxazole, 3-sulfanilamido-6-methoxy-pyridazine, 3-sulfanilamido-6-chloropyridazine, 4-sulfanilamido-2,6-dimethoxy-pyrimidine, 3-sulfanilamido-2-phenyl-pyrazole, 2-sulfanilamido-5-methyl-pyrimidine, 2-sulfanilamido-5-methoxy-pyrimidine, 2-sulfanilamido-5-methyl-isoxazole, 2-sulfanilamido-4,5-dimethyl-oxazole, 2-sulfanilamido-3-methoxy-pyrazine, 4-sulfanilamido-5,6-dimethoxy-pyrimidine, 4-sulfanilamido-3-methoxy-1,2,5-thiadiazole and 4-aminobenzene-sulfonyl-guanidine.

The compounds of the formula I can be combined with the sulfonamides mentioned by way of example, in various ratios; the ratio of the former to the latter may be from 1:10 to 5:1. However, preferred ratios are from 1:1 to 1:5. As a rule, a suitable dosage is from 20 to 500 mg of an active compound of the formula I.

To demonstrate the action of the compounds according to the invention, the latter were tested in animal experiments, using the Aronson sepsis model, infection being produced with *Streptococcus agalactiae*, and were compared with the conventional drug Trimethoprim. Groups of 30 female mice were infected with a lethal dose of *Streptococcus agalactiae* 7941 and 2 hours after infection were treated with a mixture of 300 mg of 2-sulfanilamido-4,5-dimethyloxazole + 60mg of one of the compounds according to the invention. In addition to an untreated control group, a second group was treated with a mixture—serving as a reference substance—of 300 mg of 2-sulfanilamido-4,5-dimethyloxazole + 60 mg of Trimethoprim. After 44 hours, the number of surviving animals was determined and divided by the number of survivors from the group treated with the reference substance. The numerical value thus obtained (the Trimethoprim factor) is a measure of the action of the compounds according to the invention compared to Trimethoprim. Accordingly, F=2 means that the compound is twice as active as Trimethoprim. The Table which follows shows that the compounds according to the invention exhibit up to a 5-fold superiority over Trimethoprim.

TABLE

General formula $$\text{R}^1, \text{R}^2, \text{R}^3\text{-phenyl-(CH}_2)_n\text{-[pyrimidine with NH}_2, \text{R}^4\text{]-N=C(R}^5\text{)-OR}^6$$

| No. | $R^1$ | $R^2$ | $R^3$ | $R^4$ | $R^5$ | $R^6$ | n | F |
|---|---|---|---|---|---|---|---|---|
| 1 | 4-Cl | H | H | $C_2H_5$— | $CH_3$— | $CH_3$— | 0 | 2.1 |
| 2 | 4-Cl | H | H | $C_2H_5$— | $CH_3$— | $C_2H_5$— | 0 | 5.0 |
| 3 | 4-Cl | H | H | $C_2H_5$— | $C_2H_5$— | $C_2H_5$— | 0 | 2.5 |
| 4 | 4-Cl | H | H | $C_2H_5$— | $C_3H_7$— | $C_2H_5$— | 0 | 2.4 |
| 5 | 4-Cl | H | H | H | $CH_3$— | $C_2H_5$— | 1 | 2.0 |
| 6 | 2-Cl | 4-Cl | H | H | $CH_3$— | $C_2H_5$— | 1 | 2.0 |
| 7 | 3-Cl | 4-Cl | H | H | $CH_3$— | $C_2H_5$— | 1 | 2.9 |
| 8 | 4-$CH_3$ | H | H | H | $CH_3$ | $C_2H_5$— | 1 | 1.7 |
| 9 | 4-$OCH_3$ | H | H | H | $CH_3$— | $C_2H_5$— | 1 | 1.25 |
| 10 | 3-$OCH_3$ | 4-$OCH_3$ | H | H | $CH_3$— | $C_2H_5$— | 1 | 2.0 |
| 11 | 3-$OCH_3$ | 4-$OCH_3$ | 5-$OCH_3$ | H | $CH_3$— | $CH_3$— | 1 | 2.6 |
| 12 | 3-$OCH_3$ | 4-$OCH_3$ | 5-$OCH_3$ | H | $CH_3$— | $C_2H_5$— | 1 | 1.3 |
| 13 | 3-$OCH_3$ | 4-$OCH_3$ | 5-$OCH_3$ | H | $C_2H_5$— | $C_2H_5$— | 1 | 1.4 |
| 14 | 3-$OCH_3$ | 4-$OCH_3$ | 5-$OCH_3$ | H | $C_3H_7$— | $C_2H_5$— | 1 | 1.5 |
| 15 | 3-$OCH_3$ | 4-$OCH_3$ | 5-$OCH_3$ | H | —$CH_2$—$C_6H_5$ | $C_2H_5$— | 1 | 1.5 |

Accordingly, the present invention also relates to chemotherapeutic agents which contain a compound of the formula I, in particular in combination with a sulfonamide, as the active ingredient, together with conventional carriers and excipients, and to the use of the compounds of the formula I as sulfonamide potentiators.

The chemotherapeutic agents or formulations are prepared in the conventional manner, using the conventional carriers or excipients and conventional pharmacological assistants, in accordance with the desired route of administration.

The preferred formulations are those suitable for oral administration. Examples are tablets, film tablets, dragees, capsules, pills, powders, solutions and suspensions.

EXAMPLE 1

34 g of 2,4-diamino-5-(3,4,5-trimethoxybenzyl)-pyrimidine (Trimethoprim) and 97.2 g of triethyl orthoacetate are suspended in 240 ml of dimethylformamide and 1 ml of concentrated hydrochloric acid. After stirring for 4 hours at from 80° to 90° C., the mixture is treated with active charcoal and is filtered, the filtrate is concentrated under reduced pressure and the residue is dissolved in 200 ml of warm butyl acetate. On cooling, 35.2 g (81.5% of theory) of N-[4-amino-5-(3,4,5-trimethoxybenzyl)-pyrimidin-2-yl]-acetimido-acid ethyl ester of melting point 142°–144° C. crystallize out.

The following were prepared by a method similar to that described in Example 1:

2. N-[4-Amino-5-(3,4,5-trimethoxybenzyl)-pyrimidin-2-yl]-acetimido-acid methyl ester, of melting point 171° C., from 2,4-diamino-5-(3,4,5-trimethoxybenzyl)-pyrimidine and trimethyl orthoacetate.

3. N-[4-Amino-5-(3,4,5-trimethoxybenzyl)-pyrimidin-2-yl]-propionimido-acid ethyl ester, of melting point 137° C., from 2,4-diamino-5-(3,4,5-trimethoxybenzyl)-pyrimidine and triethyl orthopropionate.

4. N-[4-Amino-5-(3,4,5-trimethoxybenzyl)-pyrimidin-2-yl]-butyrimido-acid ethyl ester, of melting point 128° C., from 2,4-diamino-5-(3,4,5-trimethoxybenzyl)-pyrimidine and triethyl orthobutyrate.

5. N-[4-Amino-5-(3,4,5-trimethoxybenzyl)-pyrimidin-2-yl]-isobutyrimido-acid ethyl ester, of melting point 136° C., from 2,4-diamino-5-(3,4,5-trimethoxybenzyl)-pyrimidine and triethyl orthoisobutyrate.

6. N-[4-Amino-5-(3,4,5-trimethoxybenzyl)-pyrimidin-2-yl]-phenylacetimido-acid ethyl ester, of melting point 168° C., from 2,4-diamino-5-(3,4,5-trimethoxybenzyl)-pyrimidine and triethyl orthophenylacetate.

7. N-[4-Amino-5-(4-methoxybenzyl)-pyrimidin-2-yl]-acetimido-acid ethyl ester, of melting point 126° C., from 2,4-diamino-5-(4-methoxybenzyl)-pyrimidine and triethyl orthoacetate.

8. N-[4-Amino-5-(3,4-dimethoxybenzyl)-pyrimidin-2-yl]-acetimido-acid ethyl ester, of melting point 148° C., from 2,4-diamino-5-(3,4-dimethoxybenzyl)-pyrimidine and triethyl orthoacetate.

9. N-[4-Amino-5-(4-methylbenzyl)-pyrimidin-2-yl]-acetimido-acid ethyl ester, of melting point 129° C., from 2,4-diamino-5-(4-methylbenzyl)-pyrimidine and triethyl orthoacetate.

10. N-[4-Amino-5-(4-chlorobenzyl)-pyrimidin-2-yl]-acetimido-acid ethyl ester, of melting point 154° C., from 2,4-diamino-5-(4-chlorobenzyl)-pyrimidine and triethyl orthoacetate.

11. N-[4-Amino-5-(3,4-dichlorobenzyl)-pyrimidin-2-yl]-acetimido-acid ethyl ester, of melting point 158° C., from 2,4-diamino-5-(3,4-dichlorobenzyl)-pyrimidine and triethyl orthoacetate.

12. N-[4-Amino-5-(2,4-dichlorobenzyl)-pyrimidin-2-yl]-acetimido-acid ethyl ester, of melting point 128° C., from 2,4-diamino-5-(2,4-dichlorobenzyl)-pyrimidine and triethyl orthoacetate.

EXAMPLE 13

29.85 g of 5-(4-chlorophenyl)-6-ethyl-2,4-diaminopyrimidine (Pyrimethamin) and 97.32 g of triethyl orthoacetate are suspended in 240 ml of dimethylformamide and 1 ml of concentrated hydrochloric acid. After stirring for 4 hours at from 85° to 100° C., the clear reaction solution is treated with active charcoal, filtered and concentrated under reduced pressure. After dissolving the residue in 100 ml of warm isopropyl ether, 32.8 g (85.2% of theory) of N-[4-amino-6-ethyl-5-(4-chlorophenyl)-pyrimidin-2-yl]-acetimido-acid ethyl ester, of melting point 143°–145° C., crystallize out.

The following were prepared by a method similar to that described in Example 13:

14. N-[4-Amino-6-ethyl-5-(4-chlorophenyl)-pyrimidin-2-yl]-acetimido-acid methyl ester, of melting point 146° C., from 5-(4-chlorophenyl)-6-ethyl-2,4-diaminopyrimidine and trimethyl orthoacetate.

15. N-[4-Amino-6-ethyl-5-(4-chlorophenyl)-pyrimidin-2-yl]-propionimido-acid ethyl ester, of melting point 124° C., from 5-(4-chlorophenyl)-6-ethyl-2,4-diaminopyrimidine and triethyl orthopropionate.

16. N-[4-Amino-6-ethyl-5-(4-dichlorophenyl)-pyrimidin-2-yl]-butyrimido-acid ethyl ester, of melting point 129° C., from 5-(4-chlorophenyl)-6-ethyl-2,4-diaminopyrimidine and triethyl orthobutyrate.

17. N-[4-Amino-6-ethyl-5-(4-chlorophenyl)-pyrimidin-2-yl]-phenylacetimido-acid ethyl ester, of melting point 120° C., from 5-(4-chlorophenyl)-6-ethyl-2,4-diaminopyrimidine and triethyl orthophenylacetate.

FORMULATION EXAMPLES 18.
400 mg of 2-sulfanilamido-4,5-dimethyloxazole
80 mg of N-[4-amino-5-(3,4,5-trimethoxybenzyl)-pyrimidin-2-yl]-acetimido-acid methyl ester (Example 2)
20 mg of corn starch
10 mg of gelatin
8 mg of talc
2 mg of magnesium stearate
20 mg of Primojel The active ingredients are mixed with corn starch and granulated, using the aqueous gelatin solution. The dry granules are sieved and mixed with the additives. This mixture is tableted in the conventional manner.

19.
160 mg of 2-sulfanilamido-5-methoxy-pyrimidine
80 mg of N-[4-amino-5-(3,4,5-trimethoxybenzyl)-pyrimidin-2-yl]-acetimido-acid ethyl ester (Example 1)
5 mg of gelatin
30 mg of corn starch
4 mg of talc
1 mg of magnesium stearate The active ingredients are granulated, using the aqueous gelatin solution, and the dried granules are mixed with corn starch, talc and magnesium stearate. This mixture is tableted in the conventional manner.

20.
400 mg of 2-sulfanilamido-4,5-dimethyloxazole
80 mg of N-[4-amino-6-ethyl-5-(4-chlorophenyl)-pyrimidin-2-yl]-acetimido-acid ethyl ester (Example 13)
20 mg of corn starch
10 mg of gelatin
8 mg of talc
2 mg of magnesium stearate
20 mg of Primojel The active ingredients are mixed with corn starch and granulated, using the aqueous gelatin solution. The dry granules are sieved and mixed with the additives. This mixture is tableted in the conventional manner.

21.
4.00 g of 2-sulfanilamido-5-methoxy-pyrimidine
2.00 g of N-[4-amino-5-(3,4,5-trimethoxybenzyl)-pyrimidin-2-yl]-acetimido-acid methyl ester (Example 2)
1.9 of Tylose C 30
30.0 g of sugar
10.0 g of glycerol
2.5 g of bentonite
0.06 g of flavoring
0.04 g of Nipagin M
0.06 g of Nipasol sodium
and 100.00 g of demineralized water The very finely milled active ingredients are suspended in the aqueous Tylose mucilage. All the other ingredients are then added successively, whilst stirring. Finally, the mixture is made up to 100.00 g with water.

We claim:

1. A N-pyrimidinyl-imidoacid ester of the general formula I $$\text{(I)}$$

where $R^1$, $R^2$ and $R^3$, which may be identical or different, are hydrogen, methyl, methoxy or chlorine, $R^4$ is hydrogen or alkyl of 1 to 4 carbon atoms, $R^5$ is alkyl of 1 to 6 carbon atoms or benzyl, $R^6$ is alkyl of 1 to 4 carbon atoms or benzyl and n is 0 or 1.

2. N-[4-Amino-5-(3,4,5-trimethoxybenzyl)-pyrimidin-2-yl]-acetimido-acid ethyl ester.

3. N-[4-Amino-5-(3,4,5-trimethoxybenzyl)-pyrimidin-2-yl]-acetimido-acid methyl ester.

4. N-[4-Amino-5-(3,4,5-trimethoxybenzyl)pyrimidin-2-yl]-propionimido-acid ethyl ester.

5. N-[4-Amino-5-(3,4,5-trimethoxybenzyl)-pyrimidin-2-yl]-butyrimido-acid ethyl ester.

6. N-[4-Amino-5-(3,4,5-trimethoxybenzyl)-pyrimidin-2-yl]-isobutyrimido-acid ethyl ester.

7. N-[4-Amino-5-(3,4,5-trimethoxybenzyl)-pyrimidin-2-yl]-phenyl-acetimido-acid ethyl ester.

8. N-[4-Amino-5-(4-methoxybenzyl)-pyrimidin-2-yl]-acetimido-acid ethyl ester.

9. N-[4-Amino-5-(3,4-dimethoxybenzyl)-pyrimidin-2-yl]-acetimido-acid ethyl ester.

10. N-[4-Amino-6-ethyl-5-(4-chlorophenyl)-pyrimidin-2-yl]-acetimido-acid ethyl ester.

11. N-[4-Amino-6-ethyl-5-(4-chlorophenyl)-pyrimidin-2-yl]-acetimido-acid methyl ester.

12. N-[4-Amino-6-ethyl-5-(4-chlorophenyl)-pyrimidin-2-yl]-propionimido-acid ethyl ester.

13. A pharmaceutical composition for treatment of systemic infectious deseases comprising a compound as set forth in claim 1, from 1:10 to 5:1 of a sulfonamide selected from the group consisting of 2-sulfanilamido-pyridine, 2-sulfanilamido-thiazole, 2-sulfanilamido-pyrimidine, 2-sulfanilamido-4-methylpyrimidine, 2-sulfanilamido-4,6-dimethyl-pyrimidine, 4-sulfanilamido-2,6-dimethyl-pyrimidine, 5-sulfanilamido-3,4-dimethyl-isoxazole, 3-sulfanilamido-6-methoxy-pyridazine, 3-sulfanilamido-6-chloropyridazine, 4-sulfanilamido-2,6-dimethoxy-pyrimidine, 3-sulfanilamido-2-phenyl-pyrazole, 2-sulfanilamide-5-methylpyrimidine, 2-sulfanilamido-5-methoxy-pyrimidine, 2-sulfanilamido-5-methyl-isoxazole, 2-sulfanilamido-4,5-dimethyl-oxazole, 2-sulfanilamido-3-methoxy-pyrazine, 4-sulfanilamido-5,6-dimethoxy-pyrimidine, 4-sulfanilamido-3-methoxy-1,2,5-thiadiazole and 4-aminobenzene-sulfonyl-guanidine, and non-toxic, therapeutically acceptable solid or liquid carriers and galenical assistants.

* * * * *